US008192430B2

(12) United States Patent
Goode et al.

(10) Patent No.: US 8,192,430 B2
(45) Date of Patent: Jun. 5, 2012

(54) DEVICE FOR EXTRACTING AN ELONGATED STRUCTURE IMPLANTED IN BIOLOGICAL TISSUE

(75) Inventors: Louis B. Goode, Cranberry Township, PA (US); Chun Kee Lui, Monroeville, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 1109 days.

(21) Appl. No.: 11/953,952

(22) Filed: Dec. 11, 2007

(65) Prior Publication Data

US 2008/0147061 A1   Jun. 19, 2008

Related U.S. Application Data

(60) Provisional application No. 60/875,231, filed on Dec. 15, 2006.

(51) Int. Cl.
*A61B 18/14* (2006.01)
*A61F 7/00* (2006.01)

(52) U.S. Cl. ............................................ 606/45; 607/99

(58) Field of Classification Search ............... 606/28, 606/39, 45–46, 108, 113; 604/95.04
See application file for complete search history.

(56) References Cited

U.S. PATENT DOCUMENTS

| 5,171,233 | A |   | 12/1992 | Amplatz et al. | 604/281 |
|---|---|---|---|---|---|
| 5,318,527 | A |   | 6/1994 | Hyde et al. | 604/95 |
| 5,562,678 | A |   | 10/1996 | Booker | 606/113 |
| 5,674,217 | A | * | 10/1997 | Wahlstrom et al. | 606/15 |
| 5,697,936 | A |   | 12/1997 | Shipko et al. | 606/108 |
| 5,769,821 | A | * | 6/1998 | Abrahamson et al. | 604/104 |
| 5,843,019 | A | * | 12/1998 | Eggers et al. | 604/22 |
| 5,980,515 | A | * | 11/1999 | Tu | 606/41 |
| 6,379,351 | B1 | * | 4/2002 | Thapliyal et al. | 606/41 |
| 6,419,674 | B1 | * | 7/2002 | Bowser et al. | 606/45 |
| 7,285,126 | B2 | * | 10/2007 | Sepetka et al. | 606/200 |
| 7,651,504 | B2 | * | 1/2010 | Goode et al. | 606/113 |
| 2004/0082868 | A1 |   | 4/2004 | Campbell et al. | 600/504 |
| 2004/0153096 | A1 |   | 8/2004 | Goode et al. | 606/113 |

OTHER PUBLICATIONS

Cook Vascular Incorporated PERFECTA® Electrosurgical Dissection System Manual, pp. 1-10, Aug. 2004.
Cook Vascular Products promotional material entitled "Pulsed Power for Lead Extraction," May 2004.

* cited by examiner

*Primary Examiner* — Michael Peffley
*Assistant Examiner* — Thomas Giuliani
(74) *Attorney, Agent, or Firm* — Brinks Hofer Gilson & Lione (57) ABSTRACT

A device for extracting an implanted elongated structure from biological tissue comprises a sheath having a plurality of lumens therein opening to the sheath distal end. First and second lumens are disposed along a wall of the sheath, and a third lumen is dimensioned to receive the elongated structure. The sheath wall having the first and second lumens disposed therein is alternately compressible and expandable responsive to a bend along a bending zone of the sheath. A first wire segment is positioned in the first lumen, and a second wire segment is positioned in the second lumen, wherein the respective proximal ends of the segments are affixed proximal to the bending zone. The respective wire segments extend distally in the respective first or second lumen a first distance beyond the distal end of the sheath when the bend compresses the wall surface generally adjacent the first and second lumens, and extend distally a second distance, less than the first distance, when the bend expands the wall surface.

20 Claims, 8 Drawing Sheets

DEVICE FOR EXTRACTING AN ELONGATED STRUCTURE IMPLANTED IN BIOLOGICAL TISSUE

RELATED APPLICATION

The present patent document claims the benefit of the filing date under 35 U.S.C. §119(e) of Provisional U.S. Patent Application Ser. No. 60/875,231, filed Dec. 15, 2006, which is hereby incorporated by reference.

BACKGROUND OF THE INVENTION

1. Technical Field

The present invention relates generally to a medical device. More particularly, the invention relates to a device for extracting an elongated structure, such as a cardiac electrical lead, that has previously been implanted in biological tissue of a human or veterinary patient.

2. Background Information

A variety of medical treatments and surgical methods entail implanting an elongated structure into the body of a human or veterinary patient. Examples of such elongated structures include catheters, sheaths and cardiac electrical leads (such as pacemaker leads and defibrillator leads), as well as a variety of other devices. Over time, it may become necessary or desirable to remove such an elongated structure from the body of the patient. However, difficulty is often encountered when attempting removal of such implanted structures, particularly after they have been implanted in biological tissue for a significant period of time.

For example, a heart pacemaker is typically implanted in a subcutaneous tissue pocket in the chest wall of a patient. A pacemaker lead is introduced into the vascular system of the patient, and positioned such that it extends from the pacemaker through a vein into a chamber of the patient's heart. The pacemaker lead commonly includes a coiled structure, such as an electrical wire coil, for conducting electrical signals (such as stimulating and/or sensing signals) between the pacemaker and the heart. Defibrillator leads are typically structured in a similar manner and, like pacemaker leads, are located about the heart. However, defibrillator leads may be affixed both internally and externally of the heart. A typical lead includes one or more coaxial or lateral helical wire coils having a hollow inner passageway that extends the entire length of the wire coil or coils. The wire coils are surrounded by an electrically insulating material such as a flexible tube, sheath or coating. The insulating material may be silicone or polyurethane, and serves simultaneously to protect the wire coils from body fluids and to insulate the wire coils from one another.

While cardiac electrical leads typically have a useful life of many years, over time such leads may become encapsulated by fibrotic tissue against the heart itself, or against the wall of the vein or other surrounding tissue. Encapsulation is especially prone to be encountered in areas where the velocity of the flow of blood is low. Since the encapsulating fibrotic tissue may be very tough, it is difficult to remove the lead from the area of the heart without causing bleeding or other trauma. Thus, for example, when small diameter veins through which a pacemaker lead passes become occluded with fibrotic tissue, separation of the lead from the vein can cause severe damage to the vein, or even destruction of the vein in some cases. Furthermore, separation of the lead from a vein is generally not possible without restricting or containing movement of the lead, that is, fixing the lead in position with respect to the patient, in particular, with respect to the patient's vein.

To avoid this and other possible complications, some inoperative pacemaker or other leads are simply left in the patient when the pacemaker or defibrillator is removed or replaced. However, such a practice can incur the risk of an undetected lead thrombosis, which can result in stroke, heart attack, or pulmonary embolism. Such a practice can also impair heart function, as plural leads can restrict the heart valves through which they pass.

There are additional reasons why removal of an inoperative lead is desirable. For example, if there are too many leads positioned in a vein, the vein can be obliterated. In addition, multiple leads may be incompatible with one another, thereby interfering with their pacemaking or defibrillating function. Of course, an inoperative lead can migrate during introduction of an adjacent second lead, and mechanically induce ventricular arrhythmia. Other potentially life-threatening complications can require the removal of the lead as well. For example, removal of an infected pacemaker lead is desirable, so as to avoid septicemia or endocarditis. Surgical removal of a heart lead in such circumstances often involves open heart surgery, with its accompanying risks, complications and significant costs.

A variety of successful methods and apparatus have been devised as alternatives to open heart surgery for heart lead removal. For example, U.S. Pat. No. 5,697,936 (Shipko et al.) discloses a device for removing from a patient a previously implanted elongated structure such as a catheter, a sheath, a defibrillator lead, a pacemaker lead or the like. The device disclosed in the patent includes a snare having one or more proximal or distal loops which can encircle and reversibly grasp either the proximal end or the distal end of the elongated structure to be removed. The device also includes a sheath member for delivering the snare loop or loops to the particular end of the elongated structure which is to be grasped. In some disclosed embodiments for grasping the distal end of the elongated structure, the sheath member is advanced along the elongated structure and separates the structure from any tissue which has encapsulated the structure after its implantation. The snare can be either positioned over or contained within a second sheath located in the sheath member.

Numerous other devices for snaring fragments or foreign bodies have been disclosed. For example, U.S. Pat. No. 5,171,233 (Amplatz, et al.) is directed to a snare-type probe in which kinking of a snare loop is obviated by the use of a shape memory material for the snare. More particularly, the snare is composed of nitinol (nickel-titanium alloy system) wire in a superelastic state, having a transition temperature below the operating temperature of the snare, for example, below body or room temperature. This allows the snare to be manipulated in a relatively severe manner during introduction into a patient, but to recover its desired shape after such manipulation, without kinking or other deformation. The loop of the snare of the device is oriented at an angle with respect to an elongate proximal member on which it is carried.

U.S. Pat. No. 5,562,678 (Booker) discloses a reversible snare for grasping and retrieving an article such as a cardiac lead, which includes a retractable closed loop carried by a sheath member adapted for introduction into a patient. The closed loop of the snare is composed of nitinol or another shape memory material, and defines a hook adapted to partly encircle the cardiac lead. The snare also includes a threader also carried by the sheath member. The threader is reversibly extendable through the closed loop, in the manner of a thread through a needle's eye, such that the hook and threader together fully encircle the lead. Retraction of the closed loop causes the hook and threader to close around the lead and permit its withdrawal into the sheath member.

U.S. Pat. No. 5,318,527 (Hyde et al.) is directed to a system for removing an in-place intravascular device (such as a catheter or guidewire) from a patient's body lumen, such as from a coronary artery, in which a catheter or other similar device is advanced through the vascular system alongside the in-place device until its distal end is located at a desired location within the vascular system. The disclosed removal system includes an exchange catheter having a flexible strand which forms a loop at the distal end of the catheter, the loop being adapted to be disposed about the catheter or guidewire that is in-place within the patient. The exchange catheter includes a lumen through which the strand passes and from which the loop extends. The exchange catheter does not appear to be dimensioned or otherwise adapted for receiving the in-place catheter or guidewire within the exchange catheter as the exchange catheter is advanced. To the contrary, it is an express purpose of the disclosed device to maintain access to a region of the body lumen about the distal end of the in-place catheter or guidewire during use of the exchange catheter, and receipt of the in-place device in the exchange catheter would interfere with the desired access to that region.

U.S. Pat. Publ. No. 2004/0153096 A1 (Goode et al.) discloses a snare-type device for removing an elongated structure that includes a sheath having a first lumen formed therein. The lumen is dimensioned to receive the elongated structure therein, and is adapted to allow advancement of the sheath along the elongated structure. The sheath also has second and third parallel lumens formed therein, such that all of the first, second and third lumens may be unitarily formed in the sheath. The device also includes a snare contained in the second and third lumens. The snare has a snare loop extending out of the second and third lumens, at and generally extending around the distal end of the first lumen. The snare loop is configured to be closeable around the elongated structure when the elongated structure is received in the first lumen of the sheath.

Each of the above-referenced devices is subject to its own advantages and disadvantages during use. For example, although the devices of Shipko et al. and Booker are generally effective for their intended purposes, these devices are somewhat more complex in structure than may sometimes be preferred, since it is often desirable to employ removal devices having a minimal cross-sectional area. The device of Amplatz et al. may require a disadvantageously high degree of axial and/or rotational manipulation before the loop can be slipped over the distal end of the device to be removed. The device of Hyde et al. purportedly avoids this particular problem by having its loop slipped over the proximal end of the in-place device and tightened about it before the exchange catheter is advanced, but not tightened about the in-place device so much that the exchange catheter cannot be readily advanced over the in-place device, or that the in-place device cannot be readily withdrawn. The device and procedure of Hyde et al. would not be useful for retrieving an elongated structure which has been left in a patient for any extended time, since encapsulation of the structure would prevent any such advancement of the exchange catheter along the structure. Moreover, kinks or surface defects or irregularities in the in-place device could make it difficult or impossible to achieve a desirably precise degree of tightening of the loop about the in-place device. Such surface defects or irregularities could result from minor amounts of encapsulating tissue which remain on the in-place device after severing of the in-place device from the bulk of the encapsulating tissue, or from defects or breakage of the in-place device itself. Finally, although the device of Goode et al. is generally effective for retrieving and removing an implanted lead, the device is not structured to have an aggressive leading end for use in cutting tissue or otherwise extracting an implanted lead from encapsulating tissue.

It would be advantageous to provide a device that is structured for extracting an implanted structure from surrounding biological tissue, and that overcomes the disadvantages existing in the art.

BRIEF SUMMARY

The problems of the prior art are addressed by the features of the present invention. In one form thereof, the invention comprises a device for extracting an implanted elongated structure from biological tissue. The device comprises a sheath having a proximal portion and a distal portion, wherein the distal portion extends to a distal end of the sheath. The sheath includes first, second and third lumens, each of the lumens opening to the sheath distal end. The first and second lumens are disposed in a wall surface of the sheath and extend generally adjacent one another along the wall surface. The third lumen is dimensioned to receive the elongated structure therein. The sheath includes a bending zone along a length thereof. The sheath wall surface having the first and second lumens disposed therein is alternately compressible and expandable responsive to a bend along the bending zone. The sheath further includes a first wire segment and a second wire segment. The first wire segment is positioned in the first lumen such that the proximal end of the first wire segment is affixed proximal to the bending zone to one of the sheath and the second wire segment. The second wire segment is positioned in the second lumen such that the proximal end of the second wire segment is affixed proximal to the bending zone to one of the sheath and the first wire segment. A remainder of the first wire segment extends distally in the first lumen, and a remainder of the second wire segment extends distally in the second lumen. The first wire segment has a length such that the segment extends distally a first distance relative to the wall surface when the bend compresses the wall surface generally adjacent the first and second lumens, and extends distally a second distance relative to the wall surface when the bend expands the wall surface generally adjacent the first and second lumens, wherein the first distance is greater than the second distance, and the distal end of the first wire segment extends distally beyond the sheath distal end at least the first distance.

In another form thereof, the invention comprises a method for extracting an implanted elongated structure from biological tissue encapsulating at least a portion of said structure in a vessel. A lead extraction device is provided. The lead extraction device comprises a sheath having a proximal portion and a distal portion, wherein the distal portion extends to a distal end of the sheath. The sheath has first, second and third lumens defined therein, each lumen opening to the sheath distal end. The first and second lumens are disposed in a wall surface of the sheath, and extend generally adjacent one another along the wall surface. The third lumen is dimensioned to receive the elongated structure therein. The sheath includes a bending zone along a length thereof. The sheath wall surface having the first and second lumens disposed therein is alternately compressible and expandable responsive to a bend along the bending zone. The sheath includes a first wire segment and a second wire segment. The first wire segment is positioned in the first lumen such that the proximal end of the first wire segment is affixed proximal to the bending zone to the sheath or the second wire segment. The second wire segment is positioned in the second lumen such that the proximal end of the second wire segment is affixed proximal to the bending zone to the sheath or the first wire segment. A remainder of the first wire segment extends distally in the first lumen, and a remainder of the second wire segment extends distally in the second lumen. The first and second wire segments each have a length such that the segments extend distally a first distance relative to the wall surface when the bend compresses the wall surface generally adjacent the first and second lumens, and extend distally a second distance relative to the wall surface when the bend expands the wall surface generally adjacent the first and second lumens, the first distance being greater than the second distance. The distal ends of the first and second wire segments extend distally beyond the sheath distal end at least the first distance. The sheath distal end is inserted into said vessel, and the sheath is advanced along one or more bends in the vessel by rotating the sheath along the bends such that the segments extend the first distance. The encapsulating tissue is cut by engaging the tissue with the segments when the segments are at the first distance.

DESCRIPTION OF PREFERRED EMBODIMENTS

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive device, as well as the axial ends of various component features. The term "proximal" is used in its conventional sense to refer to the end of the device (or component thereof) that is closest to the operator during use of the device. The term "distal" is used in its conventional sense to refer to the end of the device (or component thereof) that is initially inserted into the patient, or that is closest to the patient during use.

The present invention comprises a device for extracting an implanted elongated structure from a body vessel, such as a blood vessel, when the elongated structure is at least partially encapsulated in biological tissue. The implanted elongated structure targeted for removal may comprise a cardiac lead. As the term is used herein, a cardiac lead refers to a lead that is used in connection with a heart-related device. Non-limiting examples of cardiac leads that may be extracted from biological tissue by the inventive device include pacemaker leads, defibrillator leads, coronary sinus leads, and left ventricular pacing leads. In addition to cardiac leads, the invention may also be used in the extraction of other devices or leads, such as neurological pacing and stimulation leads. When used to extract a cardiac lead, the distal end of the cardiac lead will normally be located within the vascular system of the patient, and in particular, within a chamber of the patient's heart (such as in an atrium or ventricle of the heart). When the implanted elongated structure is a defibrillator lead, the distal end of the structure may be located either in or about the heart of the patient. The distal ends of other types of implanted elongated structures targeted for extraction may not be, and need not be, near the heart.

For convenience, the following discussion will refer to the extraction of a cardiac lead, such as a pacemaker lead. However it should be understood that this is no way intended to be a limitation on the scope of the invention, and that at least the other elongated structures referred to above may also be extracted by the inventive device. Typically, a cardiac lead comprises an inner core, comprising a cable or a coil, surrounded by a layer of insulating material. Some cardiac leads have a lumen extending therethrough, while others (i.e., "lumenless" leads) do not. The inventive device is useful for extracting implanted leads having a lumen, as well as lumenless leads.

When the inventive device is used for extraction of a cardiac lead, those skilled in the art will appreciate that the lead should initially be severed from the control device, such as a pacemaker, prior to any attempts to extract or remove the lead. The control device will normally have a much larger diameter than the remainder of the lead, and thus only an unreasonably large sheath could fit over the control device.

Figure 1:
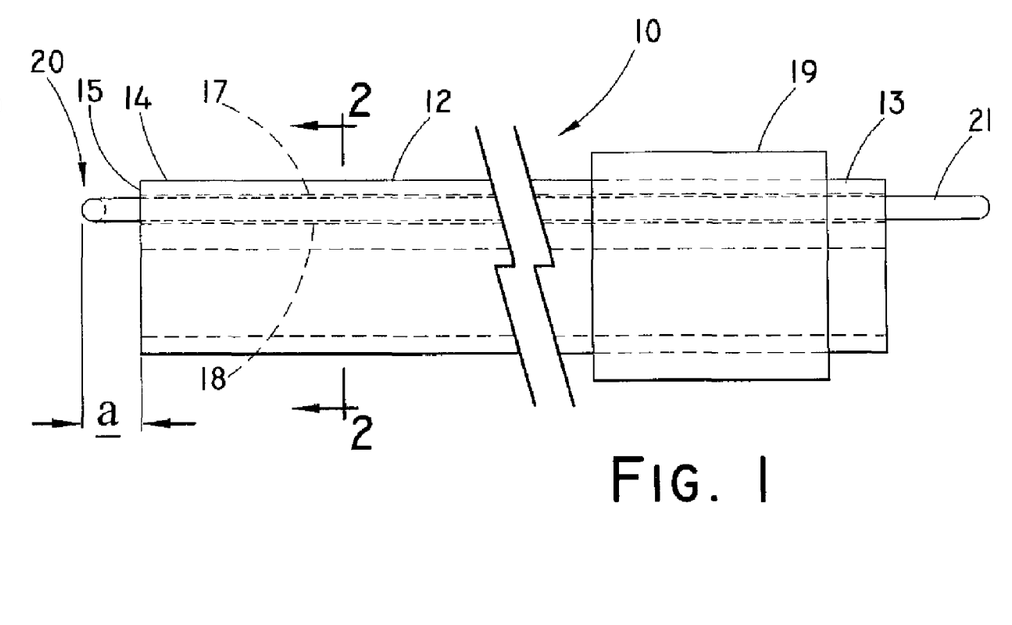
FIG. 1 is a side view of a device for extracting an elongated structure that has been implanted in biological tissue, according to one embodiment of the present invention.

The invention may be better understood with reference to the drawings. FIG. 1 illustrates a side view of an extraction device 10 according to one embodiment of the present invention. Among other possible uses, device 10 may be used for extracting an elongated structure, such as a cardiac lead, from biological tissue that has at least partially encapsulated the cardiac lead in a blood vessel. In the embodiment shown, device 10 includes an elongated sheath 12 having a proximal portion 13 and a distal portion 14. Distal portion 14 terminates in distal end 15. Sheath proximal portion 13 may be mechanically supported by an optional handle 19. Handle 19 facilitates gripping and manipulation of device 10 in well known fashion. A wire tip 20 projects in a longitudinal direction from distal end 15.

Figure 2:
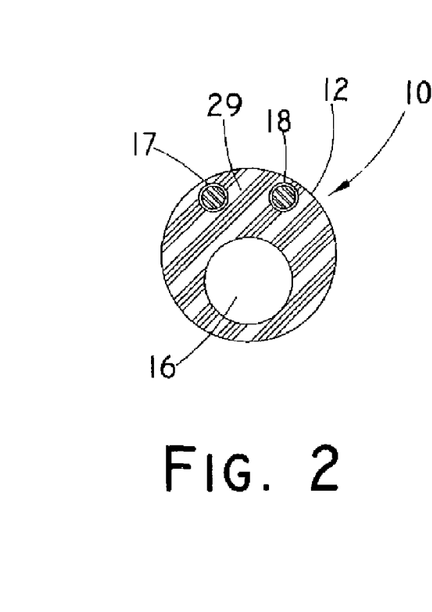
FIG. 2 is a sectional view of the sheath of the device of FIG. 1, taken along line 2-2 of FIG. 1.
Figure 3:
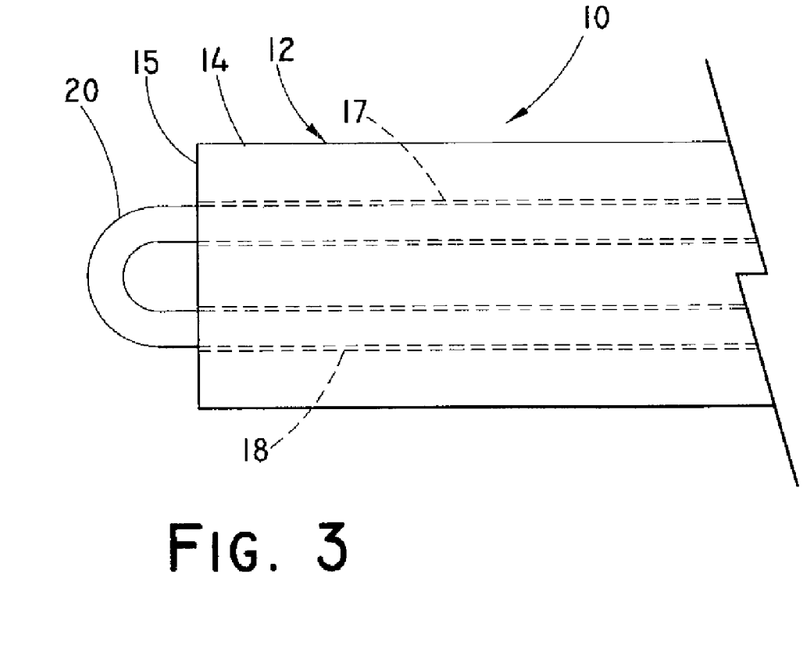
FIG. 3 is an enlarged top view of the distal end of the device of FIG. 1.
Figure 4:
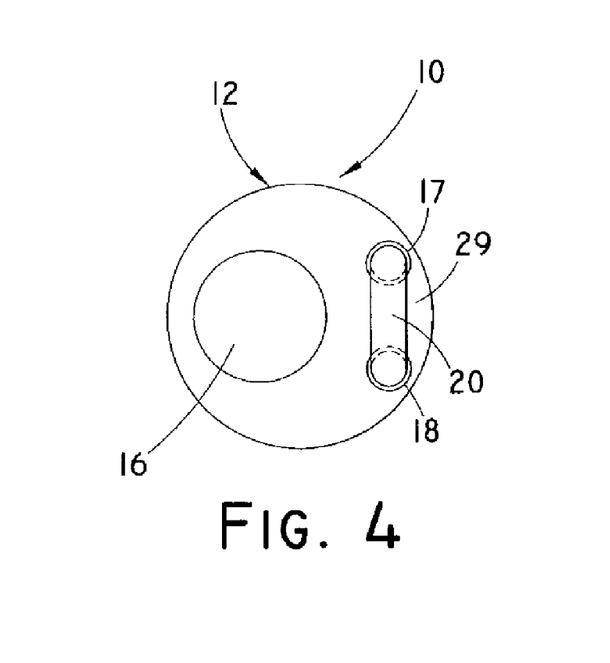
FIG. 4 is an enlarged end view of the distal end of the device of FIG. 1.

In the embodiment of FIGS. 2-4, sheath 12 is a tri-lumen sheath having a larger diameter main lumen 16, and smaller diameter lumens 17, 18. Larger diameter lumen 16 is dimensioned for receiving the elongated structure therein as extraction device 10 is advanced into the vessel. Generally, smaller diameter lumens 17, 18 are positioned adjacent each other along a wall surface 29 of sheath 12. Preferably, sheath wall surface 29 comprises a thickened area along one side of sheath 12. Sheaths used for extracting elongated structures, such as cardiac leads, are well known in the art. Those skilled in the art will appreciate that virtually any conventional sheath composition, modified as described herein, may be utilized in the inventive extraction device 10. Although sheath 12 is illustrated and described herein as a tri-lumen sheath, those skilled in the art will appreciate that with minor modification, sheaths having more, or fewer, lumens may be substituted for the tri-lumen sheath illustrated and described herein.

As stated, tip 20 extends in a generally longitudinal direction from sheath distal end 15. In the embodiment shown, tip 20 comprises a wire loop. Preferably, wire loop 20 is formed by threading a first end of a wire at the proximal end of sheath 12 through one of lumens 17, 18 until the wire exits the lumen, and therefore the sheath, at distal end 15. This end of the wire is then looped back through the other one of lumens 17, 18 until it exits the other lumen, and therefore the sheath, at proximal portion 13. The two wire ends, both extending through a separate one of lumens 17, 18 at sheath proximal portion 13, may then be twisted or otherwise joined at the proximal end to form wire end 21. Wire end 21 may be folded, adhered, or otherwise anchored to the sheath proximal end, in a manner such that longitudinal translation of wire end 21 relative to sheath proximal portion 13 is substantially prevented.

Although the embodiment of FIG. 1 illustrates an arrangement wherein the respective ends of the wire are joined at sheath proximal portion 13 to form wire end 21, such joinder of the wire ends is not required. Rather, each individual wire end may be separately folded, adhered or otherwise anchored to a discrete portion of sheath proximal portion 13 in a manner such that longitudinal translation of each of the wire ends is substantially prevented.

In FIG. 1, device 10 is shown wherein sheath 12 is in an elongated configuration. When sheath 12 is elongated in this manner, device 10 is structured such that wire tip 20 projects from the distal end a discrete distance, designated in the figures as distance a. Distance a is referred to herein as the nominal projection distance. Upon insertion of device 10 into a blood vessel in which an elongated structure, such as a cardiac lead, has previously been implanted, device 10 is often subjected to a tortuous vessel path. Frequently, the vessels that the device must traverse bend at moderate to extreme angles. Device 10 is structured such that upon bending or flexing of the device, tip 20 extends or retracts in a manner to be described.

Figure 5:
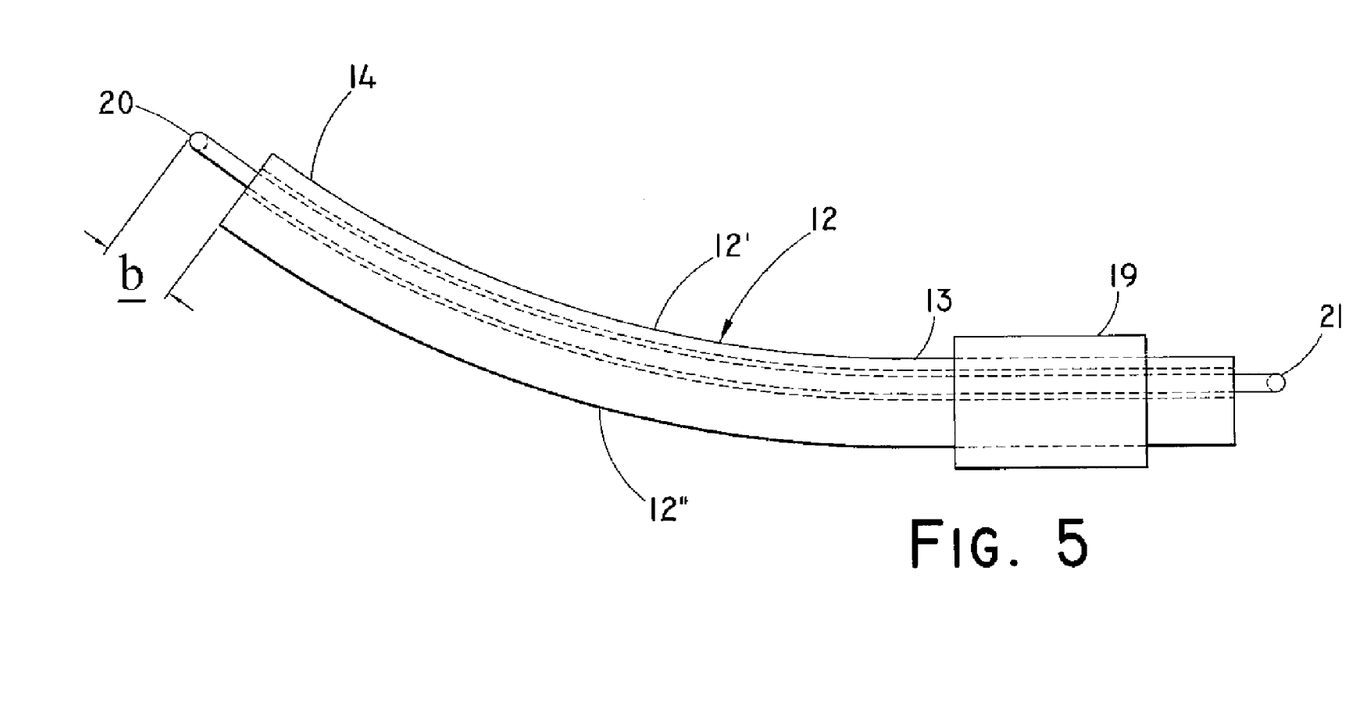
FIG. 5 illustrates one typical configuration of the sheath upon passage of the device through a branched blood vessel.

FIG. 5 illustrates one typical configuration of sheath 12 as the inventive device is passed through a branched or otherwise curved blood vessel. When passing through such a vessel, the sheath 12 flexes in conformance with the bend of the vessel. In this instance, smaller diameter lumens 17, 18 are at the inside of the bend. When the sheath is flexed in this manner, the sheath material 12' at the inside of the bend is compressed to a shorter length, when compared to the neutral axis of the sheath. The sheath material 12" at the outside of the bend is concomitantly stretched to a longer length when compared to the neutral axis. The wires, however, are neither stretched nor compressed. The proximal ends of the wires are joined to each other, or otherwise anchored to the sheath, at a position in the device proximal to the bending zone of the sheath.

As used herein, the term "bending zone" refers to the portion of the length of the sheath that is distal to the point of joinder or anchoring of the proximal ends of the wires to each other or to the sheath. This is the portion, or zone, of the sheath that is subject to bending or flexure as the sheath is advanced in the vessel, thereby causing the stretching or compressing of the sheath material as described, and the resulting retraction or extension of the wire tip from the distal end of the sheath. As shown in FIG. 5, compression of the inner sheath material 12' causes the tip 20 to project outwardly in a longitudinal direction to a distance b, which distance exceeds the nominal projection distance a shown in FIG. 1.

Figure 6:
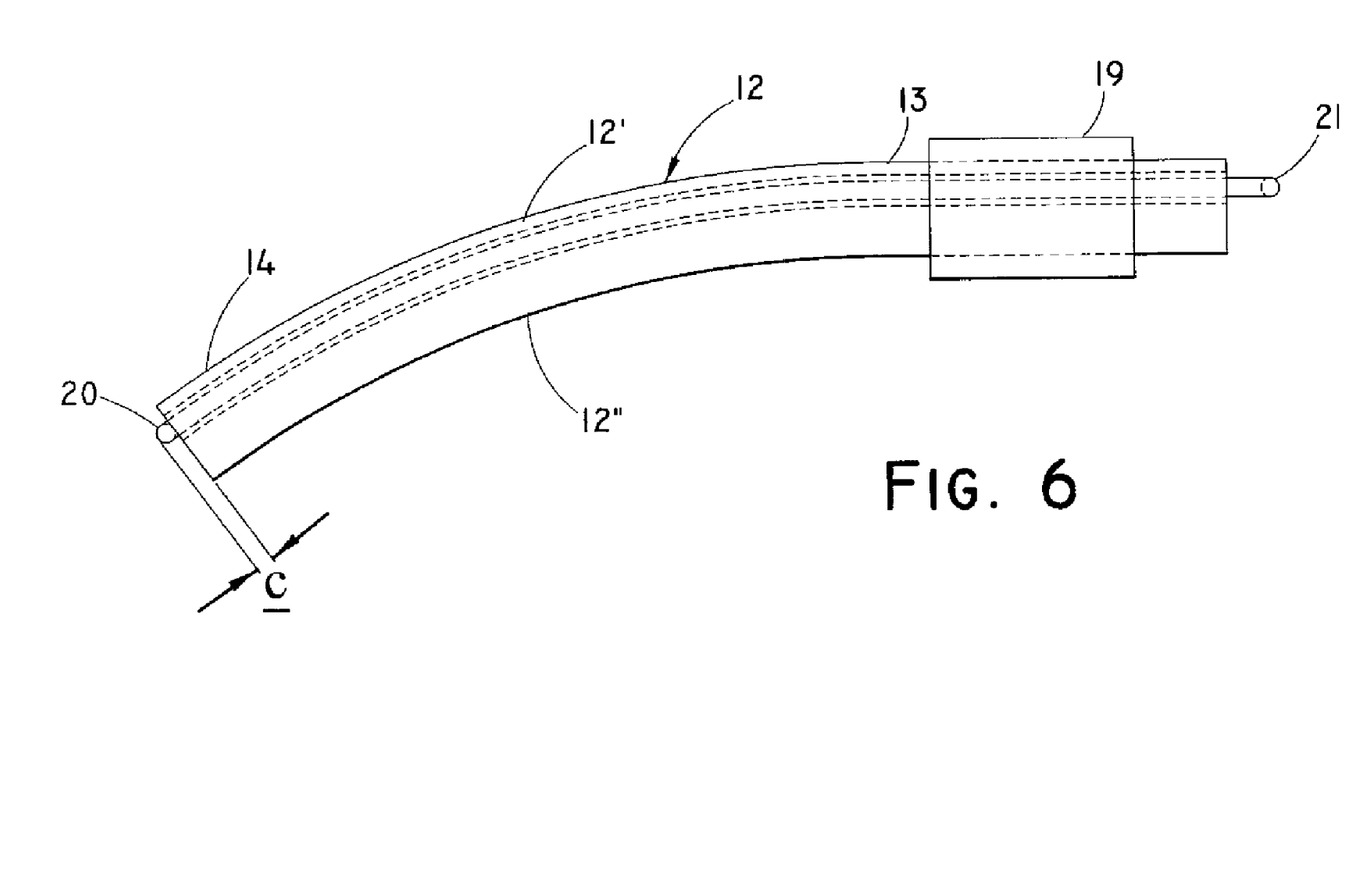
FIG. 6 illustrates a configuration of the sheath when it is flexed upon passage through a blood vessel in an opposite direction compared to the bend in FIG. 5.

FIG. 6 illustrates a configuration of sheath 12 as the inventive device is passed through a branched or otherwise curved blood vessel, wherein the curve is present in an opposite direction when compared to the curve in FIG. 5. In this case, sheath 12 is flexed in a manner such that the smaller diameter lumens 17, 18 are at the outside of the bend. When the sheath is flexed in this manner, the sheath material 12" at the inside of the bend is compressed to a shorter length, when compared to the neutral axis. The sheath material 12' at the outside of the bend is concomitantly stretched to a longer length when compared to the neutral axis. As shown in FIG. 6, stretching of the outer sheath material 12' causes the tip 20 to retract inwardly in a longitudinal direction to a minimal projection distance c, which distance is less than the nominal projection distance a of FIG. 1.

In use, device 10 is typically rotated as it is threaded through a vessel. As the device is rotated while confined to a bend in the vessel, such as the vessel resulting in the bend to the sheath shown in FIG. 5, sheath material 12' (adjacent smaller diameter lumens 17, 18) and sheath material 12" are therefore alternately at the inside of the bend during various stages of the rotation. Since the wire ends are anchored to the sheath proximal to the bend in sheath 12, the tip 20 alternately extends and retracts between respective distances b and c upon rotation of the sheath. In particular, the tip is extended to position b when the tip is oriented at the inside of the curve, and retracted to position c when it is oriented at the outside of the curve. At position b, the tip is configured to cause maximal disruption to the encapsulating tissue. At position c, the tip is configured to cause minimal disruption to the tissue. This latter arrangement minimizes the possibility of inadvertent perforation of the blood vessel.

Figure 7:
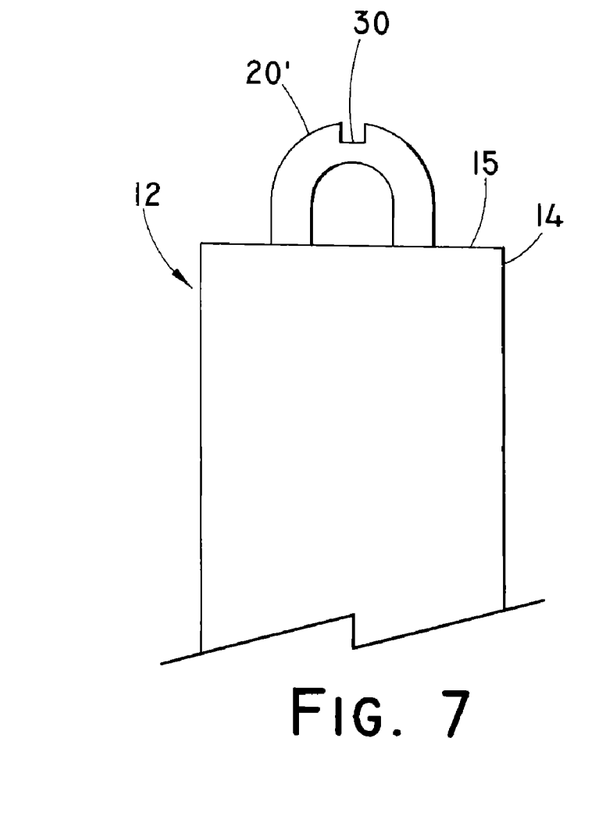
FIG. 7 is an enlarged top view of the distal end of the device of FIG. 1 illustrating a modified tip.
Figure 8:
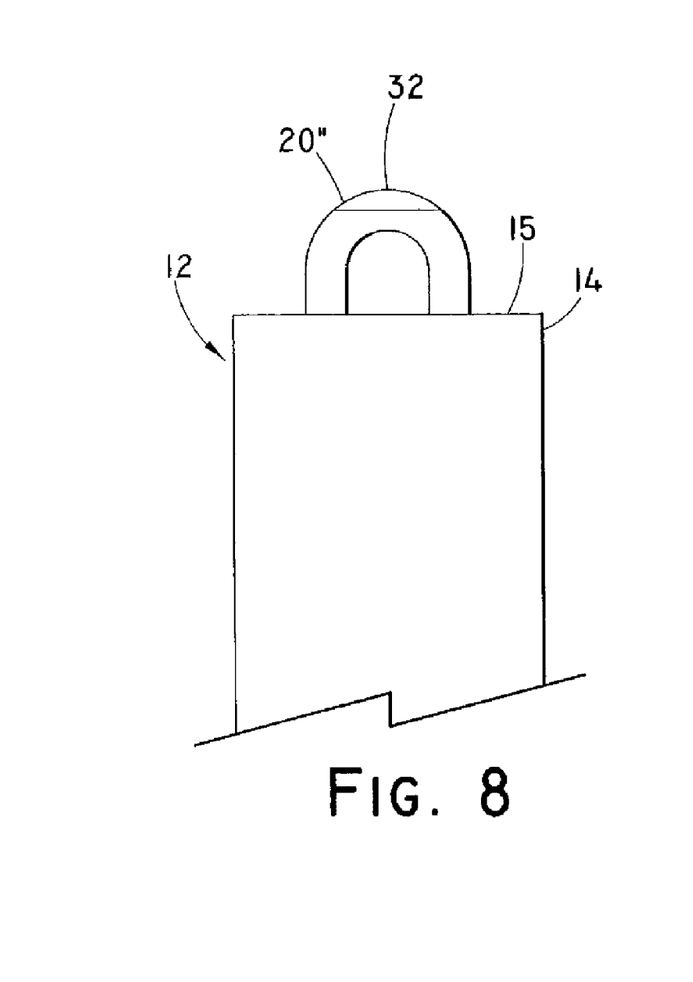
FIG. 8 is an enlarged top view of the distal end of the device of FIG. 1, illustrating yet another embodiment of a modified tip.
Figure 9:
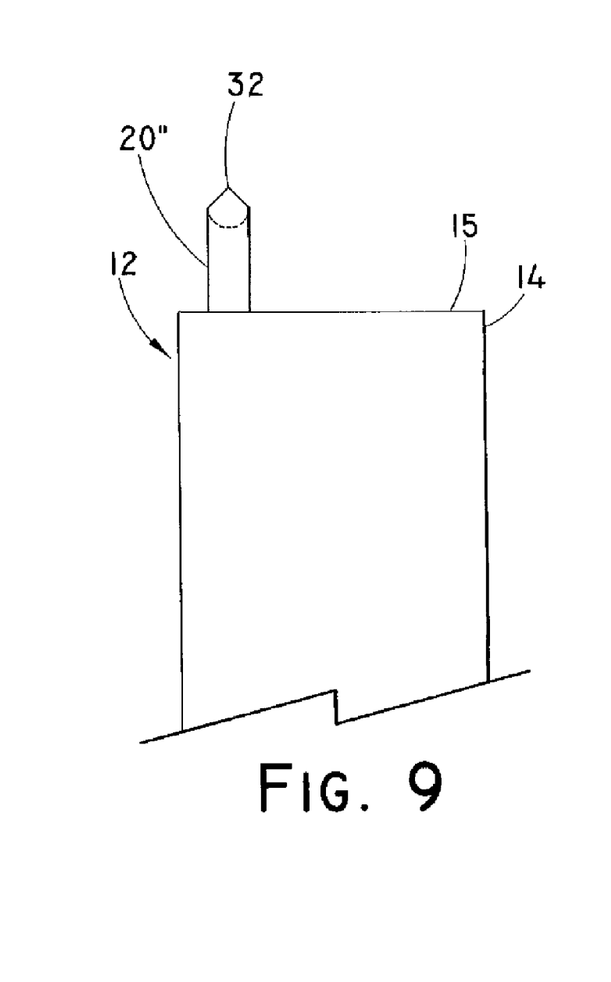
FIG. 9 is a side view of the modified tip in the embodiment of FIG. 8.

The tip in the embodiment of FIGS. 1-6 comprises a wire in which the tip is generally U-shaped. This is best shown in FIG. 3. On some occasions, it may be preferred to provide the tip with a more aggressive leading end. In this event, U-shaped tip 20 can be geometrically modified, such as by machining or forging the tip material to provide a more aggressive configuration. One example of a modified tip is shown in FIG. 7. In this embodiment, a notch 30 is cut into the loop of wire tip 20'. Another example is shown in FIGS. 8 and 9. In this embodiment, the far distal portion of tip 20" is modified by sharpening the tip to form a point 32. Those skilled in the art will appreciate that an almost infinite number of alterations of the tip can be made to make it more aggressive for a particular purpose, with the embodiments shown and described hereinabove merely representing possible examples of such alterations.

Figure 10:
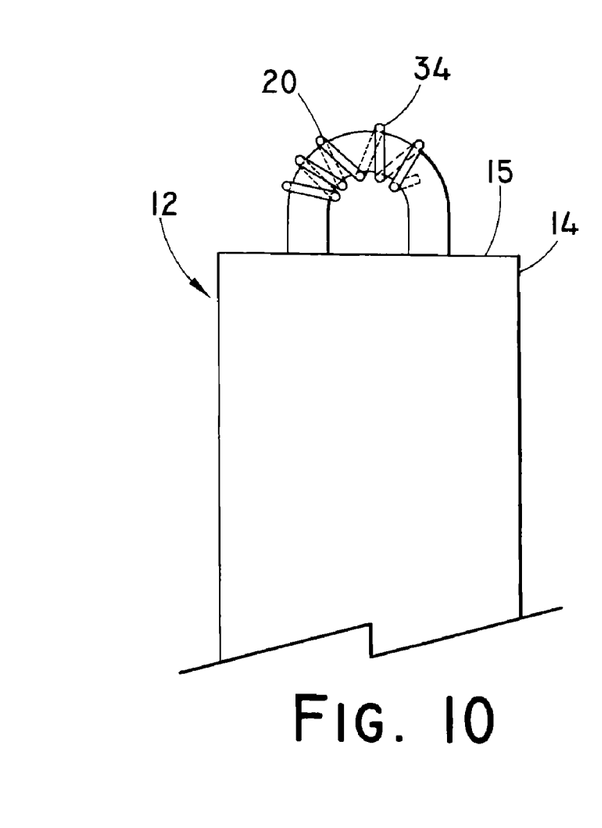
FIG. 10 is an enlarged top view of the distal end of the device of FIG. 1, illustrating an embodiment wherein a wire wrap covers the distal end of the tip.

Another variation of a tip is shown in FIG. 10. In this embodiment, a wire 34 is wrapped around tip 20. The wrapped wire may be attached to tip 20 by any conventional mechanism, such as by soldering or welding. The presence of the irregular leading end comprising the wrap provides a more aggressive end than when only the smooth loop of tip 20 is provided.

Figure 11:
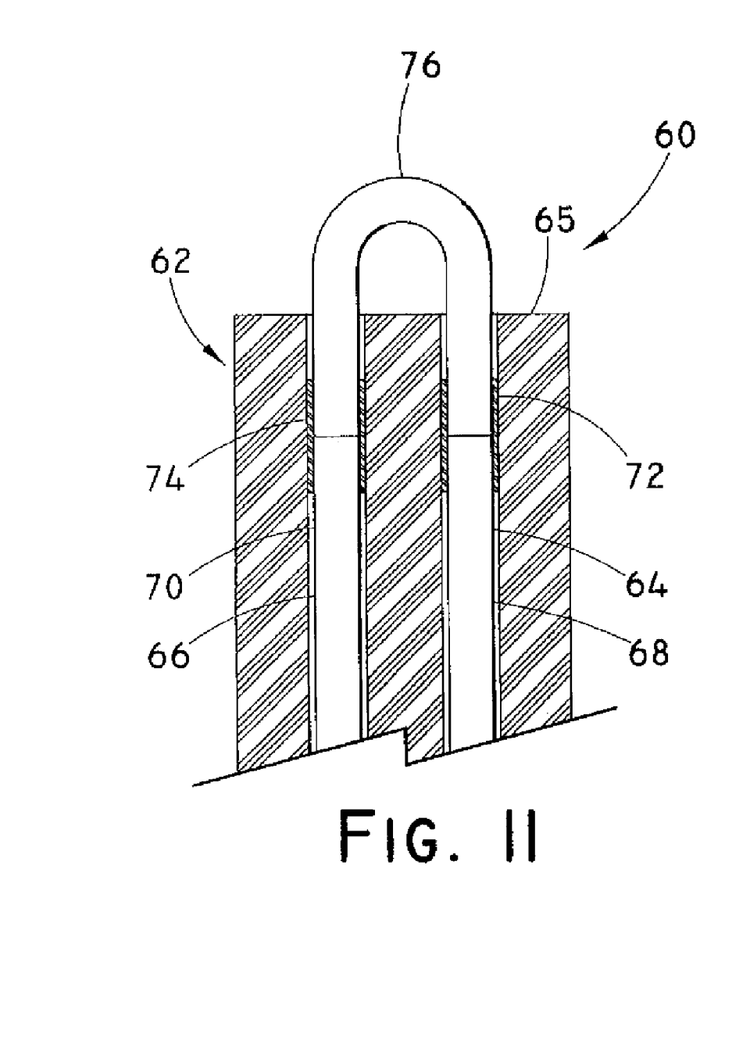
FIG. 11 is an enlarged sectional view of the distal end of an alternative embodiment of the inventive device.

Another variation of the present invention comprises device 60, as shown in FIG. 11. Device 60 may comprise a tri-lumen sheath 62 having a distal end 65 as before. A length of wire 64, 66 extends through each of smaller diameter lumens 68, 70, respectively. Attached to, and interconnecting the distal end of each of wires 64, 66 is a tip 76. In the preferred embodiment shown, tip 76 comprises a resistance or heater element. The wire ends may be attached to the resistance or heater element by any conventional attachment mechanism, such as crimps 72, 74. In this embodiment, tip 76 may be heated, e.g., by applying an electrical voltage to the proximal end of the wires. In this instance, the disruption of the tissue enveloping a cardiac lead can be enhanced if desired by simultaneous application of mechanical force and heat. Those skilled in the art will appreciate that respective wires 64, 66 and tip 76 may be formed of any compositions suitable for providing the electrically conductive properties noted. In a preferred embodiment, wires 64, 66 can be copper and tip 76 can be nichrome wire. As a further alternative, tip 76 also may be provided with an aggressive leading end, as described hereinabove.

Figure 12:
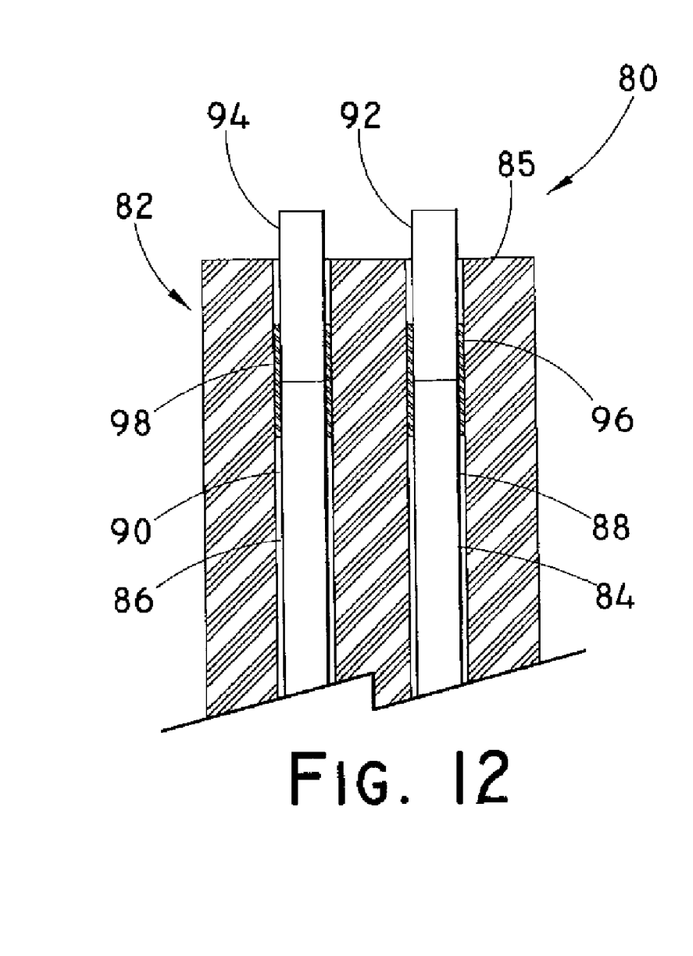
FIG. 12 is an enlarged sectional view of the distal end of yet another embodiment of the inventive device.

Another variation of the present invention comprises device 80, as shown in FIG. 12. Once again, device 80 may comprise a tri-lumen sheath 82 having a distal end 85. A length of wire 84, 86 extends through each of smaller diameter lumens 88, 90, respectively. In this embodiment, device 80 includes electrodes 92, 94, each connected to a separate one of wires 84, 86, and extending in the distal direction therefrom. In the embodiment shown, electrode 92 is connected to the distal end of wire 84 by crimp 96. Similarly, electrode 94 is connected to the distal end of wire 86 by crimp 98. Wires 84, 86 and electrodes 92, 94 are formed of any composition that is capable of conducting energy through the wires and electrodes in the distal direction, such as radio frequency energy. Preferably, wires 84, 86 are formed of copper, and electrodes 92, 94 are formed of tungsten, although those skilled in the art will appreciate that other compositions capable of attaining the desired function may also be used. With the greater protrusion of the electrodes while on the inside of a curved blood vessel (see, e.g., the bend in the sheath of FIG. 5) greater energy can be delivered to attack the enveloping tissue.

Figure 13:
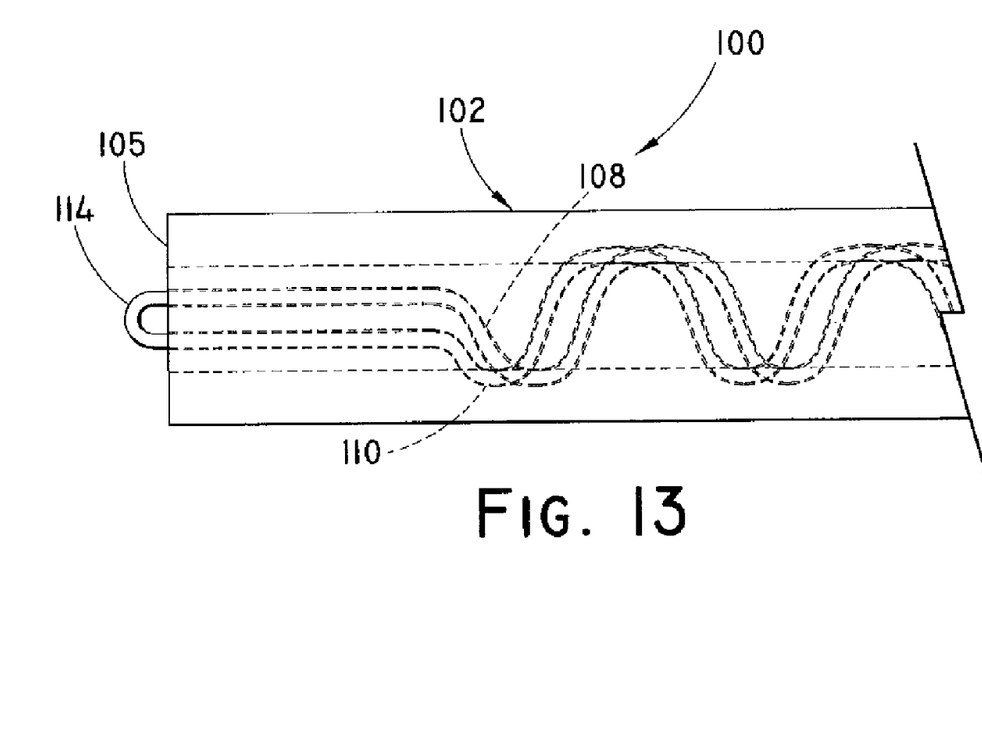
FIG. 13 illustrates another alternative embodiment of an extracting device.
Figure 14:
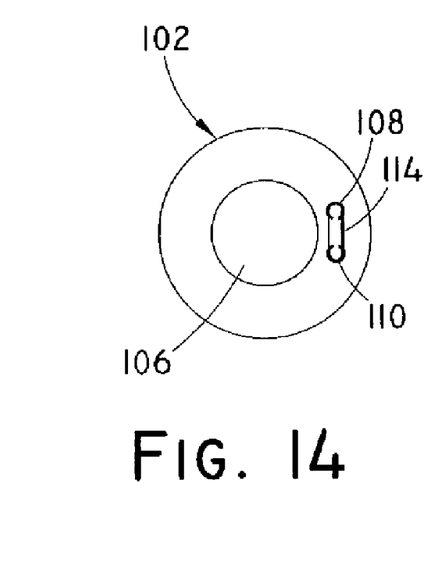
FIG. 14 is an end view from the distal end of the device of FIG. 13.

During use of an extracting device as described hereinabove, as the tip of the device progresses beyond a curve in the blood vessel, continued rotation of the sheath causes sequential extension and retraction of the tip from the distal end of the sheath, even though the tip is no longer on a curve. In some cases, however, a continued extension of the tip may not be desirable; as such rotation may increase a risk of perforating the vessel. FIG. 13 illustrates an alternative embodiment wherein the extension and retraction of the wire tip can be minimized, or even eliminated, when such action is not necessary or helpful to extracting the lead.

In this embodiment, extracting device 100 comprises a sheath, such as tri-lumen sheath 102 having a distal end 105. When a tri-lumen sheath is utilized, sheath 102 may include larger diameter lumen 106, and smaller diameter lumens 108, 110. Wire loop tip 114 extends between lumens 108, 110. In this embodiment, lumens 108, 110 wind along sheath 102 in the proximal direction from distal end 105, such as in a generally spiral fashion shown in the figure. With this configuration, extension and retraction of tip 114 only occurs while the tip is confined to a curve.

While these features have been disclosed in connection with the illustrated preferred embodiments, other embodiments of the invention will be apparent to those skilled in the art that come within the spirit of the invention as defined in the following claims.

What is claimed is:

1. A device for extracting an implanted elongated structure from biological tissue, comprising:
   a sheath having a proximal portion and a distal portion, said distal portion extending to a distal end of said sheath, said sheath having first, second and third lumens defined therein, each of said lumens opening to said sheath distal end, said first and second lumens disposed in a wall surface of said sheath and extending generally adjacent one another along said wall surface, said third lumen being dimensioned to receive the elongated structure therein, said sheath including a bending zone along a length thereof, said sheath wall surface having said first and second lumens disposed therein being alternately compressible and expandable responsive to a bend along said bending zone;
   a first wire segment and a second wire segment, each of said segments having a proximal end, said first wire segment positioned in said first lumen such that said first wire segment proximal end is affixed proximal to said bending zone to said sheath, said second wire segment positioned in said second lumen such that said second wire segment proximal end is affixed proximal to said bending zone to said sheath, a remainder of said first wire segment extends distally in said first lumen and a remainder of said second wire segment extends distally in said second lumen, said first wire segment having a length such that said segment extends distally a first distance relative to said wall surface when said bend compresses said wall surface generally adjacent said first and second lumens, and extends distally a second distance relative to said wall surface when said bend expands said wall surface generally adjacent said first and second lumens, said first distance being greater than said second distance, and said distal end of said first wire segment extending distally beyond said sheath distal end at least said first distance.

2. The device of claim 1, wherein said first wire segment and said second wire segment comprise respective segments of a unitary wire.

3. The device of claim 2, wherein respective proximal ends of said first and second segments comprise axial ends of said wire, and wherein said wire defines a loop distal to said sheath distal end, said loop extending distally a first distance when said bend compresses said wall surface generally adjacent said first and second lumens, and extending distally a second distance when said bend expands said wall surface, said first distance being greater than said second distance.

4. The device of claim 3, wherein a distal end of said loop comprises a cutting mechanism.

5. The device of claim 4, wherein said cutting mechanism is selected from the group consisting of a notch and a sharpened leading end.

6. The device of claim 3, further comprising a covering extending along at least a portion of said loop.

7. The device of claim 1, wherein said first and second wire segments are capable of conducting energy therethrough for cutting said biological tissue.

8. The device of claim 7, wherein a leading distal end of at least one of said first and second segments includes an electrode engaged thereto, said electrode capable of cutting said tissue.

9. The device of claim 8, wherein a leading distal end of each of said first and second segments includes an electrode engaged thereto, said wire segments comprising copper wire and said electrodes comprising tungsten, further comprising a respective crimp sleeve for engaging each of said first and second segments to a respective electrode.

10. The device of claim 7, wherein said first and second wire segments are joined distal to said sheath distal end to form a conductive leading end, said conductive end capable of carrying an amount of energy sufficient for cutting said tissue.

11. The device of claim 1, wherein said first and second lumens are aligned along a thickened wall of said sheath.

12. The device of claim 11, wherein said first and second lumens are aligned generally parallel along said wall.

13. The device of claim 1, wherein said first and second lumens extend in a generally spiral fashion along said sheath.

14. The device of claim 1, further comprising a handle at said proximal end of said sheath, said handle configured for facilitating at least one of gripping and manipulation of said device.

15. A method for extracting an implanted elongated structure from biological tissue encapsulating at least a portion of said structure in a vessel, comprising:

positioning a lead extraction device for insertion into said vessel, said lead extraction device comprising: a sheath having a proximal portion and a distal portion, said distal portion extending to a distal end of said sheath, said sheath having first, second and third lumens defined therein, each of said lumens opening to said sheath distal end, said first and second lumens disposed in a wall surface of said sheath and extending generally adjacent one another along said wall surface, said third lumen being dimensioned to receive the elongated structure therein, said sheath including a bending zone along a length thereof, said sheath wall surface having said first and second lumens disposed therein being alternately compressible and expandable responsive to a bend along said bending zone; a first wire segment and a second wire segment, each of said segments having a proximal end, said first wire segment positioned in said first lumen such that said first wire segment proximal end is affixed proximal to said bending zone to one of said sheath and said second wire segment, said second wire segment positioned in said second lumen such that said second wire segment proximal end is affixed proximal to said bending zone to one of said sheath and said first wire segment, a remainder of said first wire segment extends distally in said first lumen and a remainder of said second wire segment extends distally in said second lumen, said first and second wire segments each having a length such that said segments extend distally a first distance relative to said wall surface when said bend compresses said wall surface generally adjacent said first and second lumens, and extend distally a second distance relative to said wall surface when said bend expands said wall surface generally adjacent said first and second lumens, said first distance being greater than said second distance, and said distal ends of said first and second wire segments extending distally beyond said sheath distal end at least said first distance;

inserting said sheath distal end into said vessel;

advancing said sheath along one or more bends in said vessel by rotating the sheath in said one or more bends such that said segments extend said first distance; and cutting said encapsulating tissue by engaging said tissue with said segments when said segments are at said first distance.

16. The method of claim 15, wherein said first and second segments are capable of conducting energy therethrough, said method further comprising:

applying a sufficient amount of current through said segments for cutting said tissue.

17. The method of claim 15, wherein said first and second segments are joined distal to said sheath distal end to form a conductive leading end, said conductive end capable of carrying an amount of energy sufficient for cutting said tissue, said method further comprising:

applying said sufficient amount of current through said segments for cutting said tissue.

18. The method of claim 15, wherein said first wire segment and said second wire segment comprise respective segments of a unitary wire, and wherein respective proximal ends of said first and second segments comprise axial ends of said wire, and wherein said wire defines a loop distal to said sheath distal end, said loop extending distally a first distance when said bend compresses said wall surface generally adjacent said first and second lumens, and extending distally a second distance when said bend expands said wall surface, said first distance being greater than said second distance.

19. The method of claim 18, wherein a distal end of said loop comprises a cutting mechanism, and wherein said cutting mechanism is selected from the group consisting of a notch and a sharpened leading end.

20. The method of claim 15, wherein said first and second lumens are aligned generally parallel along said wall.

\* \* \* \* \*